United States Patent [19]

Greeninger et al.

[11] Patent Number: 5,324,310

[45] Date of Patent: Jun. 28, 1994

[54] CARDIAC PACEMAKER WITH AUTO-CAPTURE FUNCTION

[75] Inventors: Daniel R. Greeninger, Coon Rapids; David L. Thompson, Fridley, all of Minn.

[73] Assignee: Medtronic, Inc., Minneapolis, Minn.

[21] Appl. No.: 907,369

[22] Filed: Jul. 1, 1992

[51] Int. Cl.$^5$ .......................................... A61N 1/362
[52] U.S. Cl. ..................................................... 607/28
[58] Field of Search ................... 128/419 PG, 419 PT

[56] References Cited

U.S. PATENT DOCUMENTS

| | | | |
|---|---|---|---|
| 3,757,792 | 9/1973 | Mulier et al. | 128/419 P |
| 3,920,024 | 11/1975 | Bowers | 128/419 PG |
| 3,949,758 | 4/1976 | Jirak | 128/419 PG |
| 4,055,189 | 10/1977 | Auerbach et al. | 128/419 PG |
| 4,088,139 | 5/1978 | Auerbach | 128/419 PT |
| 4,096,865 | 6/1978 | Auerbach et al. | 128/419 PT |
| 4,114,627 | 9/1978 | Lewyn et al. | 128/419 PT |
| 4,114,628 | 9/1978 | Rizk | 128/419 PG |
| 4,144,892 | 3/1979 | Auerbach | 128/419 PT |
| 4,228,803 | 10/1980 | Rickards | 128/419 PG |
| 4,250,884 | 2/1981 | Hartlaub et al. | 128/419 PT |
| 4,305,396 | 12/1981 | Wittkampf et al. | 128/419 PG |
| 4,387,717 | 6/1983 | Brownlee et al. | 128/419 PT |
| 4,556,063 | 12/1985 | Thompson et al. | 128/419 PT |
| 4,674,508 | 6/1987 | DeCote | 128/419 PT |
| 4,674,509 | 6/1987 | DeCote, Jr. | 128/419 PT |
| 4,708,142 | 11/1987 | DeCote, Jr. | 128/419 PT |
| 4,729,376 | 3/1988 | DeCote, Jr. | 128/419 PT |
| 4,955,376 | 9/1990 | Callaghan et al. | 128/419 PG |
| 4,969,460 | 11/1990 | Callaghan et al. | 128/419 PG |
| 4,969,461 | 11/1990 | Callaghan et al. | 128/419 PG |
| 4,969,462 | 11/1990 | Callaghan et al. | 128/419 PG |
| 4,969,464 | 11/1990 | Callaghan et al. | 128/419 PG |
| 4,969,467 | 11/1990 | Callaghan et al. | 128/419 PG |
| 5,222,493 | 6/1993 | Sholder | 128/419 PG |

Primary Examiner—William E. Kamm
Assistant Examiner—Kennedy J. Schaetzle
Attorney, Agent, or Firm—Harold R. Patton; Gregory P. Gadson

[57] ABSTRACT

A pacemaker having two bipolar leads, one atrial, one ventricular, each with TIP and RING electrodes, configured as for conventional bipolar pacing/sensing in both chambers. Switching circuitry in the pacemaker is operable to select from among various possible sensing configurations, including one configuration in which sensing is performed between the ring electrodes of the respective pacing/sensing leads. Pacing is preferably performed in a conventional unipolar configuration in each chamber, from the respective tip electrodes. The "ring-to-ring" EGM signal is applied to filtering and EGM amplifier circuitry, and then provided to a telemetry system for transmission to an external receiver. The ring-to-ring EGM signal possesses the high resolution properties of conventional intracardiac signals, and is relatively unaffected by the after-potentials and tissue polarization effects that arise when the same lead is used for pacing and sensing. Additionally, the ring-to-ring EGM signal is a composite of atrial and ventricular electrical signals, and thus has an appearance similar to that of surface ECGS. In the disclosed embodiment, separate atrial and ventricular EGM amplifiers are provided, with the atrial EGM amplifier receiving a conventional atrial unipolar sensing signal and the ventricular EGM amplifier receiving a conventional ventricular unipolar sensing signal. The outputs from the respective atrial and ventricular EGM amplifiers are algebraically multiplied, and the multiplied signal is applied to a threshold detector. Capture is verified when the multiplied signal experiences a positive voltage spike that exceeds a predetermined threshold in the threshold detector.

5 Claims, 11 Drawing Sheets

CARDIAC PACEMAKER WITH AUTO-CAPTURE FUNCTION

FIELD OF THE INVENTION

This invention relates to the field of cardiac pacemakers, and more specifically to a method and apparatus for sensing electrical cardiac signals.

BACKGROUND OF THE INVENTION

Implantable cardiac pacemakers of varying degrees of sophistication and operational capability are well known in the art. Earlier pacemakers were simple by today's standards, typically being capable of pacing only in a single chamber of the patient's heart, and only at an asynchronous, fixed, and uninhibited pacing rate. Today, pacemakers are available which are capable of synchronous, inhibited pacing in both chambers, at a pacing rate which may be varied according to detected intrinsic cardiac activity or some other physiological indication of the patient's metabolic needs.

Pacemakers are most commonly operated in conjunction with one or more leads, for conveying cardiac stimulating pulses from the pacemaker to the patient's heart, and for conveying electrical cardiac signals from the heart to the pacemaker's sensing circuitry. At least two different types of pacemaker leads, unipolar and bipolar, are commonly known and used.

Unipolar leads have only a single electrode and a single electrical conductor therein. The electrode is disposed at or near the distal end of the lead, which is situated in some particular location in the patient's heart, for example at the apex of the heart in the right ventricle, in the atrial chamber, or in the coronary sinus. The single electrode and conductor of a unipolar lead are used both for sensing (that is, for conducting electrical cardiac signals from the heart to the pacemaker) and for pacing (that is, for delivering stimulating pulses from the pacemaker to the heart).

Bipolar leads have two electrodes and two electrically isolated conductors therein. Often, one electrode, called the "tip" electrode, is a conductive contact disposed at the distal end of the lead, while a second electrode, called the "ring" electrode, is a conductive ring disposed on the lead body some distance back from the distal end of the lead. One of the isolated conductors conducts signals between the pacemaker and the tip electrode, while the other conducts signals between the pacemaker and the ring electrode.

In the case of unipolar pacing and sensing, the electrically conductive pacemaker canister can serve as an indifferent electrode, with pacing and sensing signals being conducted between the lead electrode and the pacemaker canister. In bipolar pacing and sensing, it is not necessary to use the pacemaker canister as an electrode in the pacing or sensing circuit, since pacing and sensing can occur between the tip electrode and the ring electrode, rather than between the tip electrode and the pacemaker canister as in a unipolar configuration.

As pacemaker functionality has become increasingly sophisticated and complex, it has become ever more important for the physician to monitor and obtain information about the pacemaker's operation and the heart's responses to the pacing therapy. Accordingly, many pacemakers today are capable of transmitting, for example via radio-frequency telemetry, information about the pacemaker's current programmable parameter settings and the pacemaker's operational status. In addition, the telemetry system may be capable of transmitting a representation of the intracardiac electrogram (EGM). The electrical cardiac signal received on the pacemaker lead and provided to the pacemaker's sensing circuitry can also be applied to the telemetry system, and transmitted in either analog or digital form to an external receiver, where the intracardiac electrogram can be recorded and/or viewed on a strip chart or ECG monitor.

In order to verify or optimize operation of an implanted pacemaker, a physician must be able to determine, among other things, when a stimulating pulse has been delivered to a chamber of the heart, and whether the stimulating pulse possessed sufficient energy to evoke a response from that chamber of the heart (i.e., whether "capture" was achieved). Such determinations can be difficult to make, particularly with some of the more advanced dual chamber, rate-responsive pacemakers in which the pacing rate may vary from one cardiac cycle to the next, and in which stimulating pulses may or may not be delivered depending upon sensed intrinsic cardiac activity.

Often, a physician will use a conventional surface electrocardiogram (surface ECG) equipment to monitor cardiac and pacemaker functions. Obtaining a surface ECG usually requires a hospital visit, and can involve placement of a dozen or more skin electrodes. This can be uncomfortable, inconvenient, and expensive for the patient. In addition, cardiac signals are subject to attenuation and distortion when they pass through the patient's tissue to be received by surface electrodes, and this can complicate the interpretation of the signals and assessment of cardiac and pacemaker function. In some cases, the morphological aspects of an electrical cardiac signal that must be detected to accurately assess cardiac or pacemaker function are simply not revealed in the surface ECG. For example, in determining whether a pacemaker has achieved capture, the physician must look at electrical cardiac signals for evidence of an evoked cardiac response to a pacing stimulus. The electrical evidence of an evoked response is a subtle characteristic of the cardiac signal. Additionally, the stimulating pulse is often not visible in surface ECG tracings of bipolar lead configurations.

Intracardiac electrogram (EGM) signals, derived from the electrical cardiac signal on the pacemaker lead(s) and transmitted to an external programmer as described above, are also known to be useful in monitoring and verifying pacemaker operation. One perceived drawback to such intracardiac EGM signals, however, is that since the same lead is used for pacing and sensing, the high stimulating pulse voltage spike, after-potentials, and electrode-tissue polarizations render the intracardiac EGM system "blind" to the cardiac signal for a period of time immediately following the delivery of each stimulating pulse. Unfortunately, it is during this time period immediately following a stimulating pulse that is of most interest in determining whether capture has been achieved (i.e., whether there has been an evoked response).

Typically, in dual chamber pacing, atrial and ventricular EGM signals are detected using the same lead configuration (i.e., unipolar or bipolar) as used for pacing in the respective chambers. For example, if atrial bipolar pacing between the tip and ring electrodes on the atrial lead, the atrial tip and ring electrodes will also provide the inputs to the atrial sense amplifier.

With conventional surface ECG electrodes, the electrogram signal viewed by the physician on the ECG monitor or strip chart recorder represents a composite of the atrial and ventricular signals of the heart. In the inventors' experience, it has generally been found that physicians are generally more familiar with this type of ECG waveform than the separate atrial and ventricular signals provided from intracardiac electrodes. Since a surface ECG signal represents both the atrial and ventricular signals simultaneously, the physician can easily perceive the timing relationships between activity in the two chambers, the relative magnitudes of atrial and ventricular signals, and possibly evidence of an evoked cardiac response. With the separate atrial and ventricular signals provided from intracardiac electrodes, on the other hand, the physician must somehow view both signals at once, such as on a dual-trace ECG monitor or a dual-trace strip chart recorder, in order to ascertain information about the interaction or coordination of atrial and ventricular cardiac activity, and about the operation of the pacemaker. Also, intracardiac EGM signals are susceptible to the aforementioned problems with after-potentials and polarization, making detection of evoked responses difficult.

Thus, although intracardiac electrogram signals offer greater resolution (i.e., less distortion and attenuation of cardiac signals) than surface ECG signals, intracardiac pacing leads are not effective for all purposes, since the above-noted problems of after-potentials and electrode-tissue polarizations render the pacing lead "blind" to electrical cardiac activity immediately following delivery of a stimulating pulse from that lead.

The ability to detect capture in a pacemaker is extremely desirable, since delivering pacing pulses having energy far in excess of the patient's stimulation threshold is wasteful of the pacemaker's limited power supply (typically a battery). Accordingly, several different techniques for verifying capture and adjusting a pacemaker's stimulation pulse energy have been shown in the prior art.

For example, U.S. Pat. No. 3,757,792 issued to Mulier et al. on Sep. 11, 1973 and entitled "Automatic Threshold Compensating Demand Pacemaker" discloses a pacemaker in which the energy of each stimulating pulse is decreased by an incremental amount from the previous stimulating pulse. The pacemaker disclosed in the '792 patent employs three electrodes: a sensing electrode, a stimulating electrode, and a common electrode. According to the '792 patent, the common electrode must be of sufficient size to avoid after-potential and polarization problems. The pacemaker disclosed in the '792 patent monitors sensed activity during a 100-msec "window" following each stimulating pulse; if loss of capture is detected (i.e., if no intrinsic cardiac activity is detected in the 100-mSec post-stimulation time window), the pacemaker next succeeding stimulating pulse is increased in energy, but only by an amount sufficient to raise the stimulating pulse energy safely over the last stimulating pulse which did achieve capture.

U.S. Pat. No. 3,920,024 issued to Bowers on Nov. 18, 1975 and entitled "Threshold Tracking System and Method for Stimulating a Physiological System" appears to disclose a pacemaker which continuously or periodically performs a stimulation threshold test to determine the minimum energy of a stimulating pulse that will achieve capture. The stimulating pulse energy level is periodically readjusted to be very near the stimulation threshold. Intrinsic cardiac activity is monitored during a 100-mSec time window following delivery of a stimulating pulse. If capture is not achieved, one or more "back-up" pulses are delivered until an evoked response is achieved. The stimulating pulse energy level is then re-adjusted upward.

In U.S. Pat. No. 3,949,758 issued to Jirak on Apr. 13, 1976 and entitled "Automatic Threshold Following Cardiac Pacer" there appears to be disclosed a pacemaker in which the energy of each stimulating pulse is decreased from that of the previous stimulating pulse, until loss of capture is detected, whereupon the stimulating pulse energy is increased, and then the incremental decreases are resumed and the process repeated.

U.S. Pat. No. 4,055,189 issued to Auerbach et al. on Oct. 25, 1977 and entitled "Condition Monitoring Pacer", U.S. Pat. No. 4,088,139 issued to Auerbach on May 9, 1978 and entitled "Automatic Detection and Registration of Failure Condition in a Cardiac Pacer Monitoring System", U.S. Pat. No. 4,096,865 issued to Auerbach et al. on Jun. 27, 1978 and entitled "Method and Apparatus for Monitoring a Timed Failure Condition Relationship in a Cardiac Pacer", and U.S. Pat. No. 4,114,892 issued to Auerbach on Mar. 20, 1979 and entitled "Cardiac Pacer and Monitor System" are commonly-assigned patents which each appear to disclose a pacemaker having fast-recovery circuitry operable to eliminate after-potentials in a sense amplifier dedicated to monitoring capture immediately following delivery of a pacing pulse. According to the '189, '139, '865 and '892 specifications, the dedicated capture sense amplifier is thereby able to amplify any evoked response of the heart to the stimulating pulse. Cardiac signals from the pacing/sensing leads are sampled at appropriate times following delivery of a stimulating pulse, and the sampled values are compared with predetermined threshold values to determine whether an adequate evoked response has occurred. If an insufficient evoked response (or no evoked response) is detected more than a predetermined number of times in a row, the pacemaker responds by increasing the energy of stimulating pulses, and by generating a marker pulse that can be recorded on a surface ECG.

U.S. Pat. No. 4,114,627 issued to Lewyn et al. on Sep. 19, 1978 and entitled "Cardiac Pacer System and Method with Capture Verification Signal" discloses a pacemaker having circuitry that is said to remove electrode polarization energy from the input of the pacemaker's sense amplifier, so that sensing can resume very shortly (18-mSec, according to the '627 specification) after a stimulating pulse is delivered. Thus, the pacemaker described in the '627 patent is said to be capable of detecting capture even though only a single lead is used for both pacing and sensing functions.

U.S. Pat. No. 4,114,628 issued to Rizk on Sep. 19, 1978 and entitled "Demand Pacemaker With Self-Adjusting Threshold and Defibrillating Feature" appears to disclose a pacemaker having an electromechanical transducer adapted to detect a ventricular contraction following delivery of a stimulating pulse. The pacemaker circuitry increments a counter upon delivery of stimulating pulse. If a ventricular response to the stimulating pulse is detected by the electromechanical transducer during the refractory period after the stimulating pulse, the counter is decremented. If no response is detected, the counter is not decremented. The energy level of pacing pulses varies according to the count value of the counter; thus, if one or more stimulating pulses are delivered without a corresponding ventricular response, the energy level of subsequent pacing pulses will be increased in response to the positive, non-zero count value in the counter.

U.S. Pat. No. 4,228,803 issued to Rickards on Oct. 21, 1980 and entitled "Physiologically Adaptive Cardiac Pacemaker" apparently discloses a pacemaker having a first sense amplifier for detecting QRS complexes, and a second sense amplifier for detecting T-waves (i.e., a ventricular evoked response). According to the '803 specification, the pacemaker varies its base pacing rate in proportion to the time interval between a delivered stimulus and an evoked response (T-wave) thereto. If no evoked response is detected, the stimulating pulse energy is incrementally increased. The '803 specification further describes a magnet mode in which pacing stimuli are delivered at an asynchronous rate with maximum energy. When the magnet is removed, the pacemaker reduces the stimulating pulse energy in a sequence of steps in successive cycles, until a pacing pulse is delivered which does not evoke a response. Then, the pacing energy is increased one step.

U.S. Pat. No. 4,305,396 issued to Wittkampf et al. on Dec. 15, 1981 and entitled "Rate Adaptive Pacemaker and Method of Cardiac Pacing" relates to a pacemaker having so-called "polarization compensation circuitry" that is said to produce a compensation signal that is combined, via a differential adder, to the sense amplifier inputs. According to the '396 specification, this compensation signal is said to counter the effects of electrode polarization, so that QRS complexes and T-waves can be accurately sensed following delivery of a stimulating pulse. The '396 specification also describes an initial, positive-going excursion of each stimulating pulse, followed by the conventional negative-going stimulating pulse itself. The initial, positive-going portion of the stimulating pulse is said to further compensate for the effects of electrode polarization.

U.S. Pat. No. 4,674,508 issued to DeCote on Jun. 23, 1987 and entitled "Low-Power Consumption Cardiac Pacer Based on Automatic Verification of Evoked Contractions", U.S. Pat. No. 4,674,509 issued to DeCote, Jr. on Jun. 23, 1987 and entitled "System and Method for Detecting Evoked Cardiac Contractions", U.S. Pat. No. 4,708,142 issued to DeCote, Jr. on Nov. 24, 1987 and entitled Automatic Cardiac Capture Threshold Determination System and Method", and U.S. Pat. No. 4,729,376 issued to DeCote, Jr. on Mar. 8, 1988 and entitled "Cardiac Pacemaker and Method Providing Means for Periodically Determining Capture Threshold and Adjusting Pulse Output Level Accordingly" are commonly-assigned patents which relate to a capture determination scheme. According to these patents, a capture detect circuit is provided which is said to operate based on an assumption that if pacing pulses are applied to the heart in closely-spaced pairs, only one of the two pulses can possibly evoke a cardiac response. Furthermore, according to these patents, if the first pulse of the pair is delivered at an energy level known to exceed the patient's capture threshold, then this first pulse will evoke a response, and the second one of the pair will not. The capture verification circuit described in these patents digitizes the "recovery artifact" (i.e., the electrode polarization occurring after a pacing pulse) following the second pacing pulse of the pair. According to these specifications, the digitized recovery artifact will be the same for any pacing pulse which does not evoke a response. Thereafter, only single pacing pulses need to be delivered; the recovery artifact following each pacing pulse is then compared to the digitized recovery artifact from the non-capture pacing pulse. Only recovery artifacts from other pacing pulses that did not evoke a response will match the digitized recovery artifact; a pacing pulse which does evoke a response will differ from the digitized artifact, and this detection of this difference indicates that capture has been achieved.

U.S. Pat. No. 4,955,376 issued to Callaghan et al. on Sep. 11, 1990 and entitled "Pacemaker With Improved Automatic Output Regulation", U.S. Pat. No. 4,969,460 issued to Callaghan et al. on Nov. 13, 1990 and entitled "Pacemaker With Improved Automatic Output Regulation", U.S. Pat. No. 4,969,461 issued to Callaghan et al. on Nov. 13, 1990 and entitled "Pacemaker With Improved Automatic Output Regulation", U.S. Pat. No. 4,969,462 issued to Callaghan et al. on Nov. 13, 1990 and entitled "Pacemaker With Improved Automatic Output Regulation", U.S. Pat. No. 4,969,464 issued to Callaghan et al. on Nov. 13, 1990 and entitled "Pacemaker With Improved Automatic Output Regulation", and U.S. Pat. No. 4,969,467 issued to Callaghan et al. on Nov. 13, 1990 and entitled "Pacemaker With Improved Automatic Output Regulation" (hereinafter collectively referred to as the Callaghan et al. patents.) are commonly-assigned patents which relate to a pacemaker said to be capable of automatic capture verification and pacing threshold determination. According to the Callaghan et al. patents, a "charge dump" circuit is provided for discharging polarization potentials on the output capacitor and electrode immediately after delivery of each pacing pulse. Pacing is peformed between the tip electrode of a bipolar pacing/sensing lead and the pacemaker canister, serving as a common or indifferent electrode. Sensing of intrinsic cardiac actitivity is performed in conventional bipolar manner (i.e., between the tip and ring electrodes of the bipolar lead). Sensing of cardiac activity following delivery of a pacing pulse, on the other hand, is performed between the ring electrode and the pacemaker canister.

According to the Callaghan et al. patents, a capture detection circuit is coupled to the ring electrode and is activated during a 60-mSec time window following delivery of pacing pulse. Capture verification is normally performed every four cardiac cycles; if capture is not detected upon capture verification, the pacing rate is temporarily increased by 5-PPM, in order to determine whether the apparent loss of capture is actually the result of a fusion beat (i.e., a simultaneous instrinsic and paced event). If the possibility of a fusion beat is ruled out, the stimulating pulse energy in increased incrementally until capture is obtained (and the energy is further increased to provide a safety margin between the stimulation threshold and the pulse energy.

Notwithstanding the variety of prior art arrangements for enabling a pacemaker to verify capture, it is believed by the inventors that there has yet to be shown in the prior art a method for verifying capture that is well-suited to dual-chamber pacemakers.

For example, many of the above-noted prior art references relating to capture verification (e.g., Mulier et al. '792, Bowers '024, Jirak '758, Auerbach et al. '189, and '865, Auerbach '139 and '892, Lewyn et al. '627, Rizk '628, Rickards '803, Wittkampf et al. '396, DeCote '508, '509, '142, and '376, and Callaghan et al. '376, '460, '461, '462, '464, and '467) appear to address only single-chamber (specifically, ventricular) pacing and sensing.

It appears to the inventors that in the prior art, the problems with electrode polarization and after-potentials has been dealt with primarily in two ways: either additional circuitry is required to quickly counteract such after-potentials following a stimulation pulse, or an additional electrode or lead is required that is dedicated to the capture sensing function. The additional circuitry is considered undesirable, since it itself consumes some power, and increases the size and complexity of the pacemaker's circuitry. A lead dedicated to the capture sensing function is also considered undesirable, particularly with dual-chamber pacemakers which already require two leads. Lastly, none of the above methods is totally without problems as no successful commercial product has been developed based upon the above patents.

SUMMARY OF THE INVENTION

In view of the foregoing considerations relevant to pacemaker pacing and sensing and the desirability of monitoring cardiac electrical activity, pacemaker operation, and capture verification, it is believed by the inventors that there has yet to be shown in the art a pacing and sensing arrangement that fully addresses the various perceived shortcomings of known techniques.

It is accordingly a feature of the present invention that a pacemaker is provided with the ability to reliably verify capture.

It is another feature of the present invention that no electrode or lead dedicated exclusively to the capture sensing function is required.

It is still another feature of the present invention that no additional circuitry is required to counteract the effects of post-stimulation after-potentials and electrode polarization.

In accordance with the present invention a pacemaker having two bipolar leads (i.e., one atrial, one ventricular, each with TIP and RING electrodes) is implanted in a patient. The leads are configured as for conventional bipolar pacing/sensing in both chambers. Switching circuitry in the pacemaker is operable to select from among various possible sensing and/or pacing configurations, including one configuration in which sensing is performed between the ring electrodes of the respective pacing/sensing leads. Pacing is preferably performed in a conventional unipolar configuration in each chamber, from the respective tip electrodes. The "ring-to-ring" EGM signal is applied to filtering and EGM amplifier circuitry, and then provided to a telemetry system for transmission to an external receiver. The ring-to-ring EGM signal possesses the high resolution properties of conventional intracardiac signals, and is relatively unaffected by the after-potentials and tissue polarization effects that arise when the same lead is used for pacing and sensing. Additionally, the ring-to-ring EGM signal is a composite of atrial and ventricular electrical signals, and thus has an appearance similar to that of surface ECGS.

Further in accordance with the present invention, the switching circuitry is also operable to connect the atrial tip and ring electrodes to the two inputs of an atrial differential sense amplifier, and to connect the ventricular tip and ring electrodes to the two inputs of a ventricular differential sense amplifier. The respective outputs from the atrial and ventricular amplifiers are then multiplied to produce a composite sensing signal from which capture can be readily verified. The switching circuitry can couple the pacemaker canister to the atrial and ventricular sense amplifier inputs in place of the respective atrial and ventricular ring electrodes to produce a similar composite sensing signal.

BRIEF DESCRIPTION OF THE DRAWINGS

The foregoing and other aspects of the present invention will be best understood with reference to the following detailed description of a specific embodiment of the invention, when read in conjunction with the accompanying drawings, wherein.

DETAILED DESCRIPTION OF A SPECIFIC EMBODIMENT OF THE INVENTION

Figure 1A:
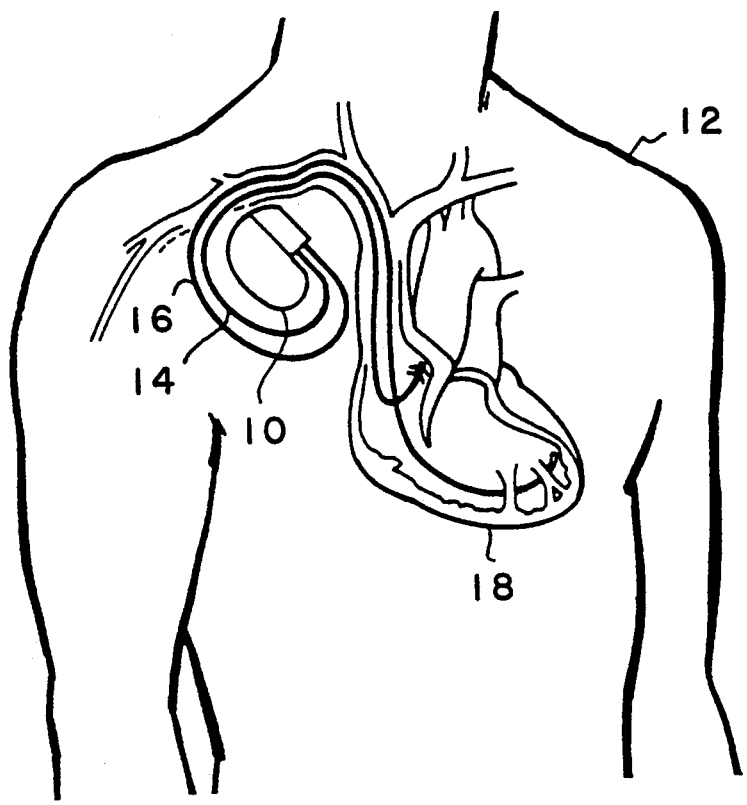
FIG. 1a is an illustration of a pacemaker and pacemaker leads in accordance with one embodiment of the present invention, implanted in a patient.

In FIG. 1a, a pacemaker 10 in accordance with one embodiment of the present invention is shown implanted in a patient 12. Transvenous atrial and ventricular leads 14 and 16, respectively, conduct signals between the heart 18 and pacemaker 10, in a conventional manner.

Figure 1B:
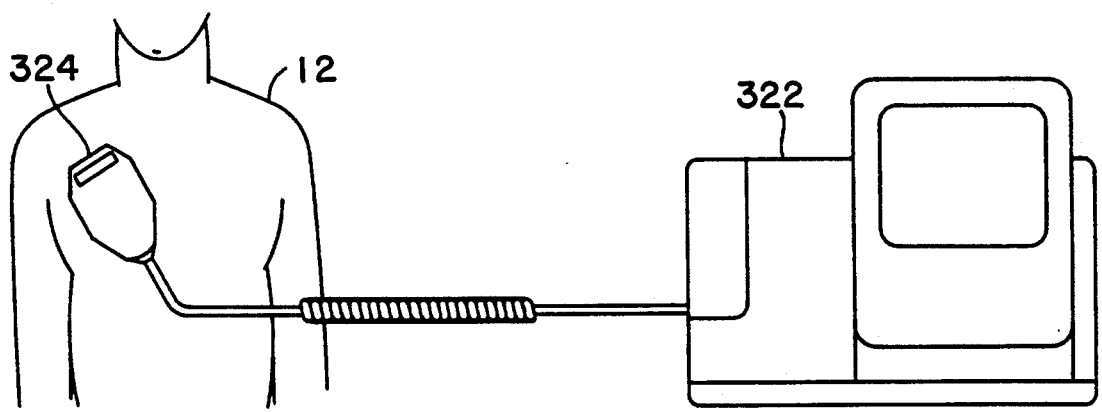
FIG. 1b is an illustration of an implanted pacemaker and external programmer in accordance with a second embodiment of the present invention.

In FIG. 1b, an external programmer 322 is shown, with a handheld programming "wand" 324 positioned over patient 12 in a conventional manner. In this configuration, an RF communications link between implanted pacemaker 10 (not visible in FIG. 1b) and programmer 322 can be established.

Figure 2:
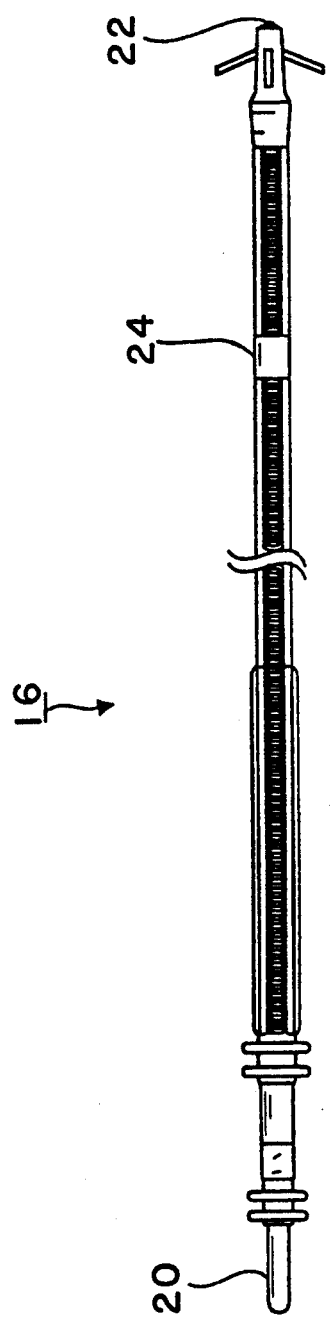
FIG. 2 is an enlarged view of a pacemaker lead from FIG. 1.

FIG. 2 is a somewhat enlarged view of bipolar ventricular lead 16 from FIG. 1. On its proximal end, lead 16 has a connector pin 20 adapted to be received in a connector block on pacemaker 10, in a manner well known in the prior art. A "tip" electrode 22 is disposed on the extreme distal end of lead 16, and at least one "ring" electrode 24 is disposed some distance back from the distal end along the body of lead 16. Bipolar atrial lead 14 is substantially the same as lead 16, except that atrial lead 14 is commonly provided with a "J" shape at its distal end to facilitate the disposition of the lead 14 within the atrium of the heart. A great many bipolar implantable pacing/sensing electrodes have been shown in the prior art that are suitable for the purposes of the present invention, and it is believed by the inventors that selection and use of a particular type of bipolar lead is not critical to the present invention. One lead suitable for the purposes of the present invention is the Model 4012 lead manufactured by and commercially available from Medtronic, Inc., Minneapolis, Minn.

For the purposes of the present description of a particular embodiment of the invention, the cardiac signals received by leads 14 and 16 shall be referred to as follows: the signal received at the tip electrode of ventricular lead 16 will be designated VTIP, and the signal at the ring electrode of ventricular lead 16 will be designated VRING; similarly, ATIP and ARING will be used to designate the signals received at the tip and ring electrodes, respectively, of atrial lead 14. To the extent that the pacemaker canister is included in the pacing/sensing arrangement as a common or indifferent electrode, the electrical signal associated with the pacemaker canister will be designated CASE.

Figure 3:
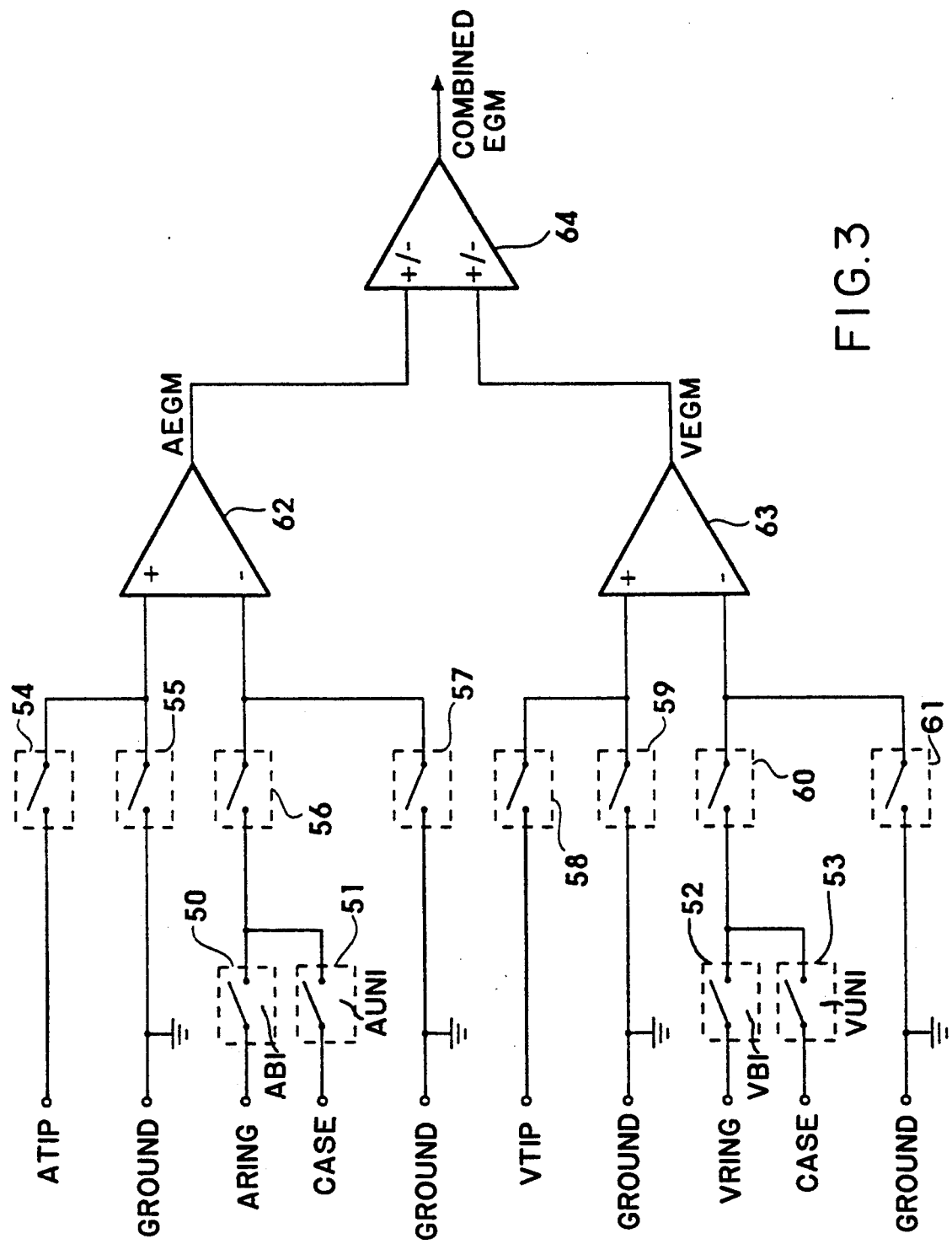
FIG. 3 is a schematic diagram of a portion of the circuitry in the pacemaker of FIG. 1.

Turning now to FIG. 3, EGM circuitry from the pacemaker 10 of FIG. 1a is shown in schematic form. It is to be understood that the present invention may be practiced in the context of many different pacemakers presently known and commercially available, such as the Medtronic Elite ™. Pacemaker 10 should include a telemetry system capable of transmitting an analog EGM signal to an external receiver; such a telemetry system is disclosed, for example, in U.S. Pat. No. 4,556,063 issued to Thompson et al. on Dec. 3, 1985 and entitled "Telemetry System for a Medical Device", which patent is hereby incorporated by reference in its entirety.

As shown in FIG. 3, the circuitry therein is coupled to the ATIP, ARING, VTIP, VRING, and CASE signals previously described with reference to FIGS. 1a and 2; the circuit is also coupled to ground at several points, as shown in the Figure. The circuitry of FIG. 3 includes a plurality of switches 50 through 61. It is to be understood, of course, that switches 50 through 61 may be implemented in a number of ways, although in the presently preferred embodiment, these switches are implemented as simple transistors in an integrated circuit, as will be hereinafter shown in greater detail with reference to FIG. 7. In addition, it is contemplated that switches 50 through 61 will not be physically actuated, but instead will be actuated under control of software or hardware in the control circuitry of pacemaker 10. For the purposes of the following description, each one of the switches 50 through 61 will be described as being "open" when it is in the position shown in FIG. 3, while a switch which establishes a connection between its terminals will be described as "closed".

The circuit of FIG. 3 further includes an atrial EGM amplifier 62, a ventricular EGM amplifier 63, and a combined EGM amplifier 64. EGM amplifiers are well-known in the pacemaker field, and it is believed by the inventors that the present invention may be practice in conjunction with many different types of EGM amplifiers, such as that disclosed in the above-reference Thompson '063 patent. The output of combined EGM amplifier 64 is available to be applied to the pacemaker's telemetry system for transmission to an external receiver. As previously noted, the telemetry system may be of the type described in the above-referenced Thompson et al. patent.

Switches 50 and 51 in FIG. 3 are provided to allow selection of either atrial unipolar or atrial bipolar sensing in pacemaker 10. Similarly, switches 52 and 53 are provided to allow selection of either ventricular unipolar or ventricular bipolar sensing in pacemaker 10. As previously noted, controlling the status of switches 50 through 53 is preferably accomplished under control of the hardware or software associated with the pacing control circuitry of pacemaker 10; thus, for example, a command issued from an external programmer indicating that atrial bipolar sensing is to be performed would cause the pacemaker's control circuitry to activate certain of the transistor(s) comprising switches 50 and 51, so that switch 50 is closed and switch 51 is open. Switches 50 and 51 and switches 52 and 53 may be independently controlled, so that, for example, atrial unipolar and ventricular bipolar sensing may be selected.

With the arrangement of switches 50 through 61 shown in FIG. 3, there are a number of possible combinations of sensing signals which can be made. These combinations are summarized in the following Table 1:

TABLE 1

| AEGM | SWITCHES | | | | VEGM | SWITCHES | | | | COMBINED EGM |
|---|---|---|---|---|---|---|---|---|---|---|
| | 54 | 55 | 56 | 57 | | 58 | 59 | 60 | 61 | |
| ATIP TO GROUND | Closed | Open | Open | Closed | VTIP TO GROUND | Closed | Open | Open | Closed | ATIP-VTIP |
| ARING TO GROUND | Open | Closed | Closed | Open | VRING TO GROUND | Open | Closed | Closed | Open | ARING-VRING |
| ATIP TO ARING/CASE | Closed | Open | Closed | Open | VTIP TO VRING/CASE | Closed | Open | Closed | Open | SUMMED |
| ATIP TO ARING/CASE | Closed | Open | Closed | Open | GROUND TO GROUND | Open | Closed | Open | Closed | AEGM |
| GROUND TO GROUND | Open | Closed | Open | Closed | VTIP TO VRING/CASE | Closed | Open | Closed | Open | VEGM |
| ARING/CASE TO GROUND | Open | Closed | Closed | Open | GROUND TO GROUND | Open | Closed | Open | Closed | ARING |

As will be hereinafter described, it is the configuration of switches 50 through 61 which results in an ARING-VRING signal, or an ATIP-VTIP signal, being produced at the COMBINED EGM output of the circuitry of FIG. 3 that is of particular relevance to the presently disclosed embodiment of the invention.

Figure 4:
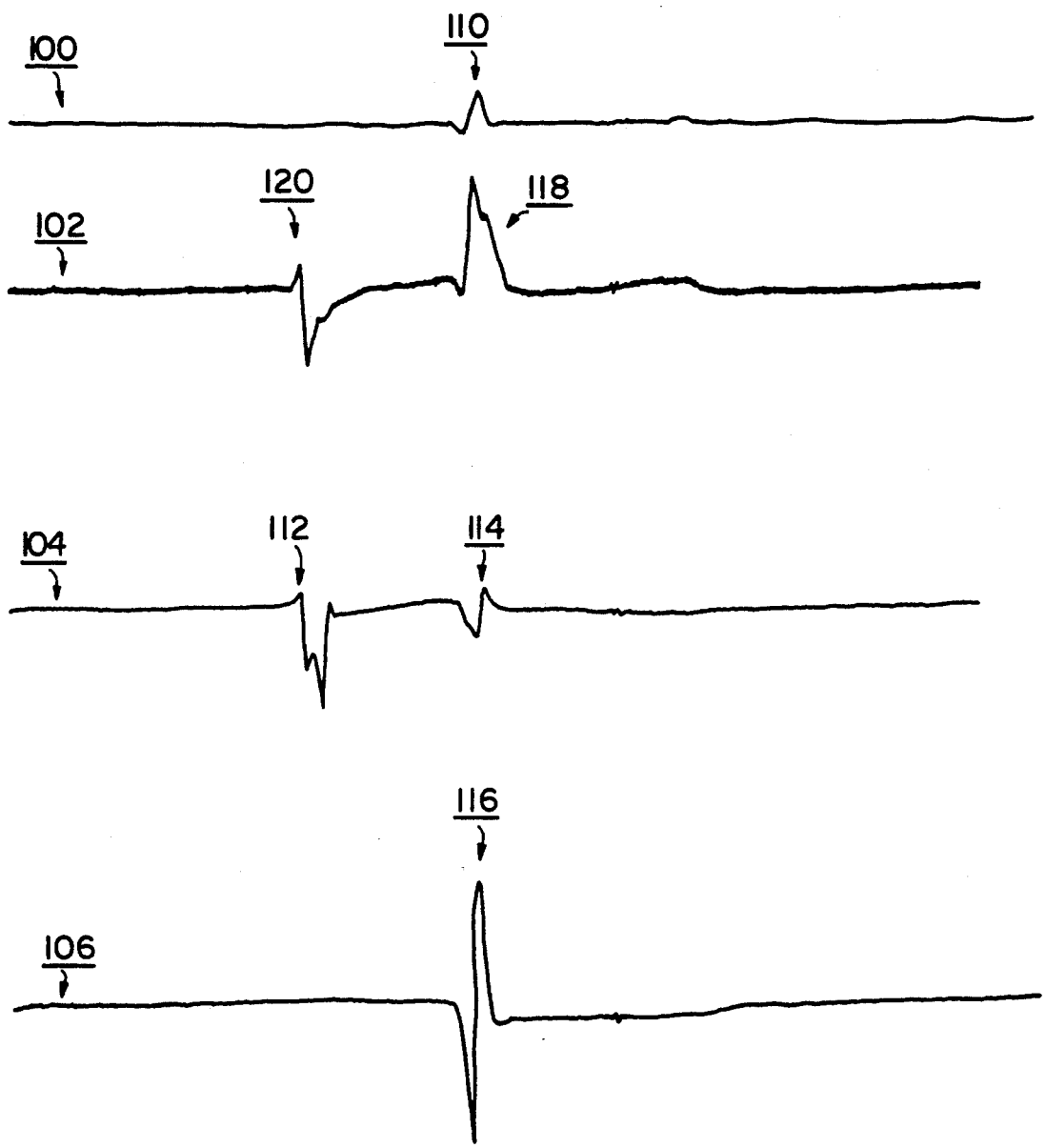
FIG. 4 is a set of electrical cardiac signal waveforms conducted on the pacemaker lead from FIGS. 1 and 2.

Turning now to FIG. 4, a graph of various cardiac waveforms is shown. In FIG. 4 and later Figures, it is to be understood that the several waveform traces in each Figure are time-synchronized, such that a given horizontal position in the Figures corresponds to the same time in each of the waveforms depicted.

In FIG. 4, a first waveform 100 corresponds to the surface ECG signal taken from a patient using conventional surface electrodes. Waveform 100 is what most physicians are accustomed to seeing and analyzing. A QRS complex designated generally as 110 in FIG. 4 is the most pronounced feature of the surface ECG signal, and the P-wave and T-wave phases of the cardiac signal are barely discernable, if at all.

Waveform 104 in FIG. 4 corresponds to the ATIP-ARING sensing configuration commonly available with prior art pacemakers; this signal corresponds to the voltage between the atrial tip and ring electrodes. The more prominent feature of waveform 104 is the atrial (P-wave) phase of the cardiac cycle, designated generally as 112 in FIG. 4. A so-called "far-field R-wave" (FFR) 114 is also visible in waveform 104, this corresponding to the detection of ventricular activity in the atrial channel. Far-field R-waves are visible in the atrial channel because ventricular signals typically are of a much greater magnitude than atrial signals, and conduction of these relatively large signals through the heart tissue and blood from the ventricle to the atrium allows the QRS complex to be detected by an atrial lead. Atrial signals, being of relatively smaller magnitude, are typically not detected by a ventricular lead; thus, there is typically no "far-field P-wave" visible in the ventricular channel.

Waveform 106 in FIG. 4 corresponds to the voltage between the ventricular tip and ring electrodes (VTIP to VRING sensing). The ventricular signal (QRS-complex) is designated 116 in waveform 106, and as previously noted, little if any atrial activity is received by the ventricular lead.

Waveform 102 in FIG. 4 corresponds to the VRING to ARING sensing configuration in accordance with the presently disclosed embodiment of the invention. Note in waveform 102 that both a well-defined ventricular QRS-complex 118 and a well-defined atrial P-wave 120 are visible, thus enabling a physician to derive more information from waveform 102 than from either waveform 100, waveform 104, or waveform 106.

Figure 5:
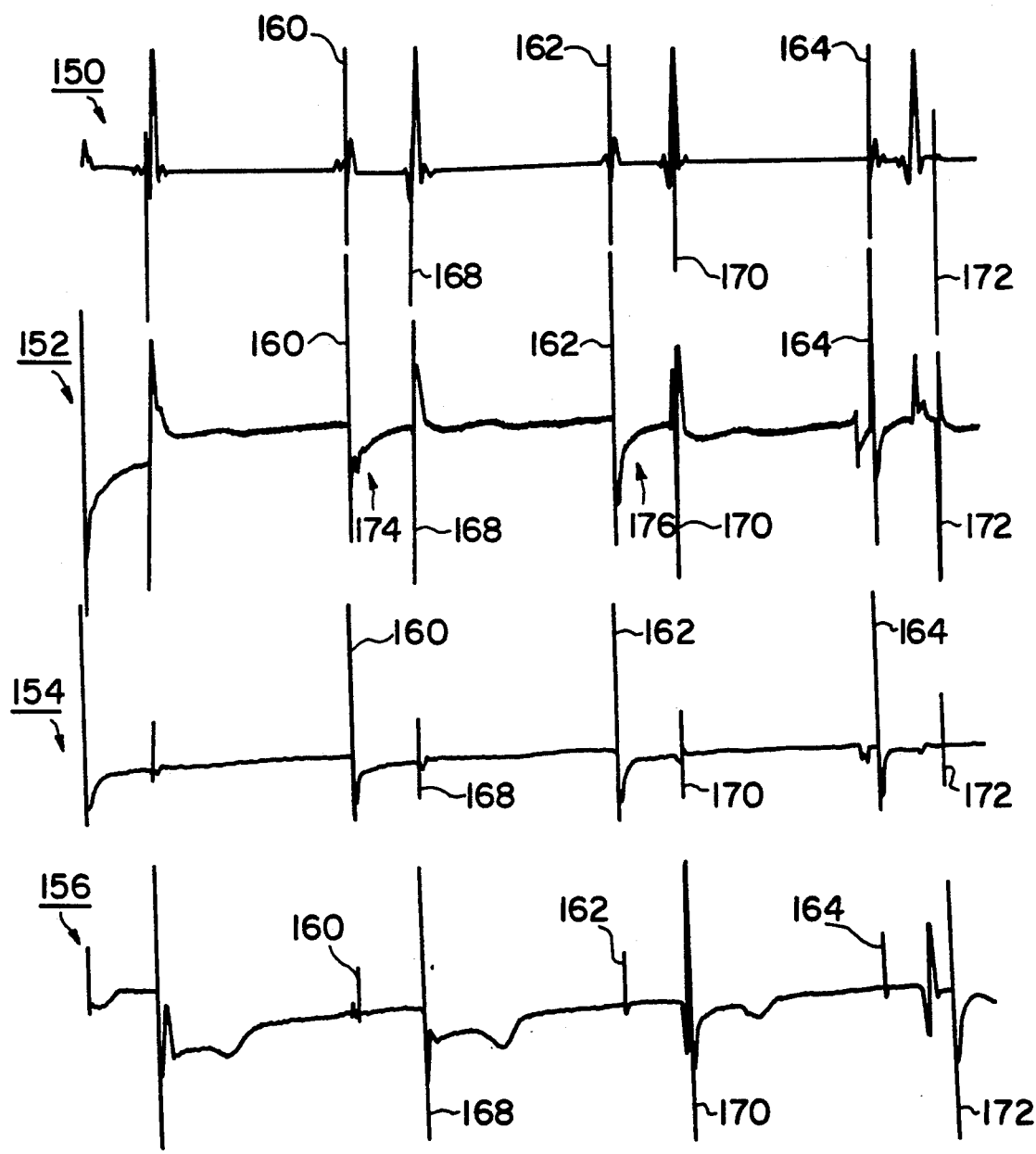
FIG. 5 is another set of electrical cardiac signal waveforms conducted on the pacemaker lead from FIGS. 1 and 2.

In FIG. 5, another set of cardiac waveforms is shown. Waveform 150 corresponds to a surface ECG signal from the patient. Waveform 154 is an ATIP-ARING (atrial bipolar sensing) signal, waveform 156 is a VTIP-VRING (ventricular bipolar sensing) signal, and waveform 152 is an ARING-VRING signal. In the sequence of cardiac cycles depicted in the waveforms of FIG. 5, pacemaker 10 is delivering atrial and ventricular pacing pulses at an asynchronous, uninhibited rate with a programmed A-V delay of 150-mSec. In each of the waveforms 150, 152, 154, and 156, the atrial pacing pulses are designated as 160, 162, and 164. Ventricular pacing pulses are designated as 168, 170 and 172. In the ATIP-ARING waveform 154, provided from the atrial TIP and RING electrodes, atrial pacing pulses 160, 162, and 164 appear to have a greater magnitude than ventricular pacing pulses 168, 170, and 172, since the atrial lead is in much closer proximity to the atrium than the ventricular lead is. Little or no information about ventricular activity is discernible from waveform 154. In VTIP-VRING waveform 156, atrial pacing pulses 160, 162, and 164 appear to have a much lower magnitude than ventricular pacing pulses 168, 170, and 172, the ventricular lead being in closer proximity to the ventricle than the atrial lead. Little or no information about atrial activity is discernible from waveform 156.

In the surface electrode waveform 150 in FIG. 5, both atrial and ventricular pacing pulses are visible. However, as would be apparent to one of ordinary skill in the art of cardiac signals, little can be determined about evoked cardiac responses to stimulating pulses in surface electrode waveform 150. On the other hand, from ARING-VRING waveform 152, an evoked atrial response 174 to atrial stimulating pulse 160 is discernible, whereas it is not in either of waveforms 150, 154, or 156. Moreover, the lack of an evoked atrial response at 176 to atrial stimulating pulse 162 can also be seen in waveform 154, whereas the presence or absence of an evoked response to stimulating pulse 162 cannot be determined in the other waveforms.

Figure 6:
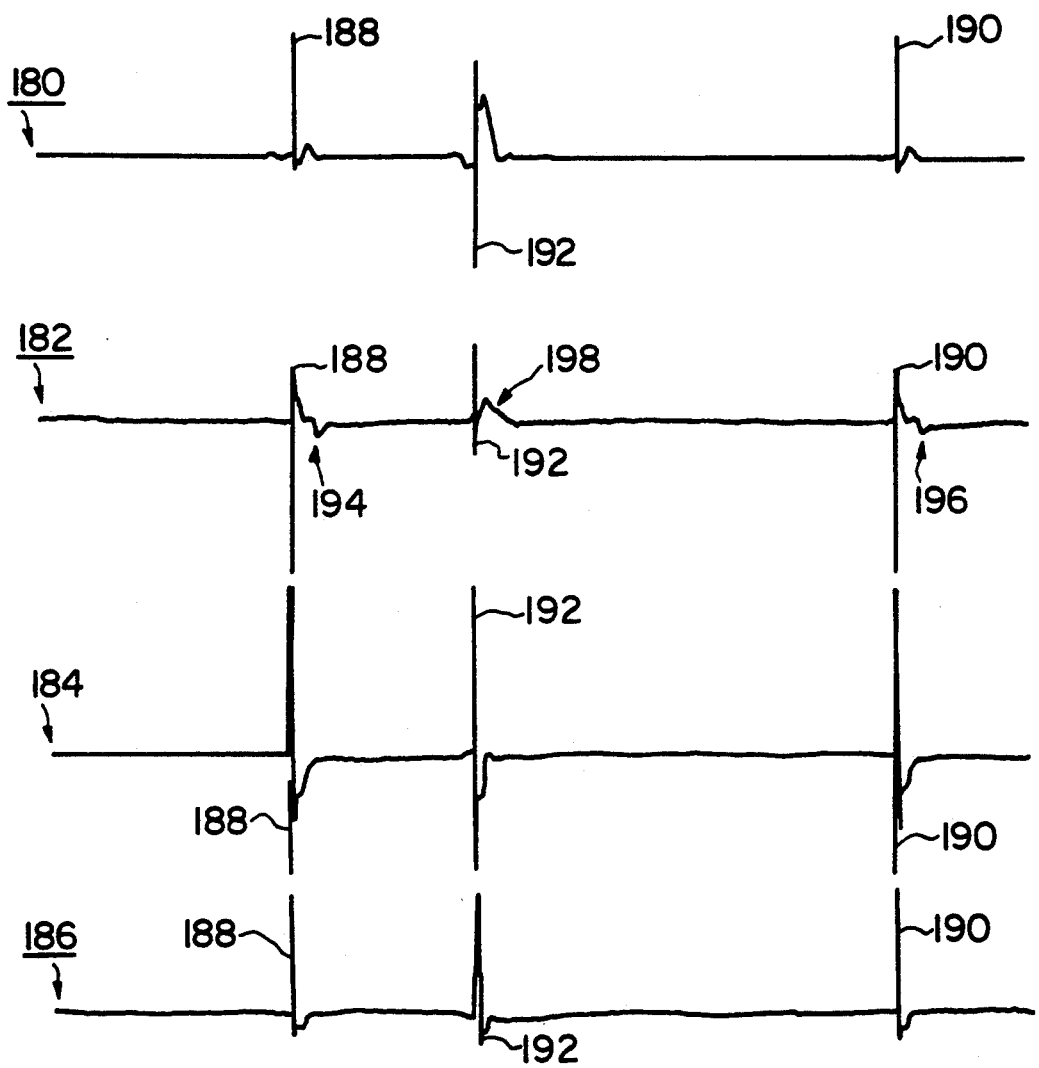
FIG. 6 is another set of electrical cardiac signal waveforms conducted on the pacemaker lead from FIGS. 1 and 2.

Turning now to FIG. 6, still another set of EGM waveforms is shown, where waveform 180 is a surface ECG signal, waveform 184 is an ATIP-CASE (unipolar atrial sensing) signal, waveform 186 is a VTIP-CASE (unipolar ventricular sensing) signal, and waveform 182 is an ARING-VRING signal. In FIG. 6, atrial pacing pulses 188 and 190 are shown, and ventricular pacing pulse 192 is shown. In the unipolar sensing waveforms 184 (atrial unipolar) and 186 (ventricular unipolar), evoked responses to stimulating pulses 188, 190, and 192 cannot be discerned. However, in ARING-VRING waveform 182, an evoked atrial response 194 to atrial stimulating pulse 188 is visible, an evoked atrial response 196 to atrial stimulating pulse 190 is visible, and an evoked ventricular response 198 to ventricular stimulating pulse 192 is visible.

Figure 7:
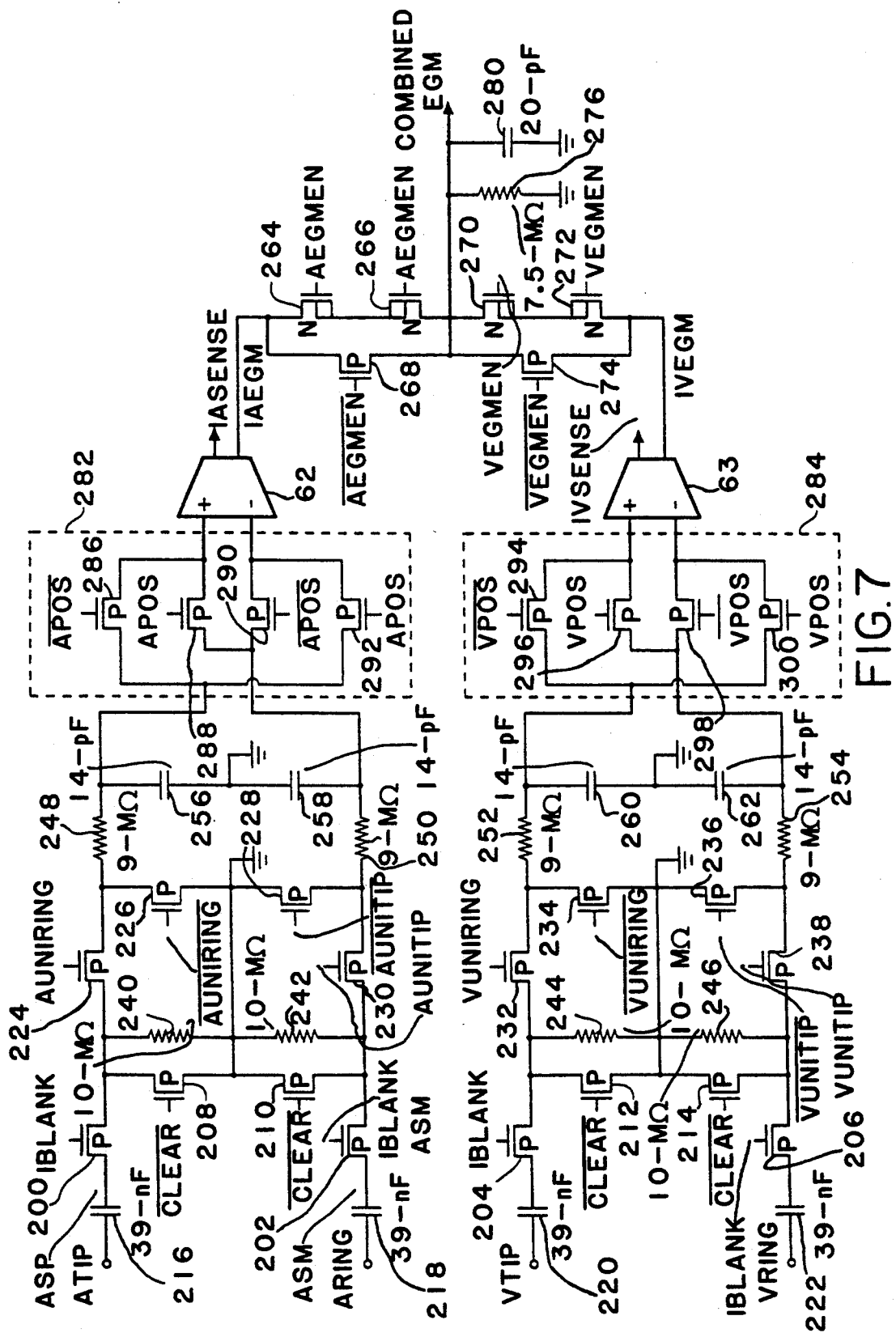
FIG. 7 is a schematic diagram of a specific embodiment of switching circuitry from FIG. 3.

Referring to FIG. 7, a schematic diagram of a specific implementation of a portion of the circuitry of FIG. 3 is shown. The circuitry of FIG. 7 is preferably implemented as part of an integrated circuit, but may also be implemented using discrete components.

In FIG. 7, transistors 200, 202, 204, and 206 are gated by a signal IBLANK to disconnect the EGM circuitry including EGM amplifiers 62 and 63 from the TIP and RING electrodes during delivery of pacing pulses and during the fast recharge cycle of the pacing output capacitors. This prevents amplifiers 62 and 63 from saturating.

Transistors 208, 210, 212, and 214 in FIG. 7 are gated by a signal $\overline{\text{CLEAR}}$ which is asserted (negative) along with IBLANK to hold the inputs to amplifier 62 and 63 at ground when TIP and RING are disconnected therefrom. Transistors 208, 210, 212, and 214 remain conductive slightly longer than transistors 200, 202, 204, and 206 (i.e., $\overline{\text{CLEAR}}$ is asserted slightly longer than IBLAN-K during pace and fast recharge) to allow 39-nF capacitors 216, 218, 220, and 222 to be cleared of any voltage which may have accumulated during pace and recharge.

Transistors 224 and 226 are gated by signals AUNIRING and $\overline{\text{AUNIRING}}$ (it being understood that $\overline{\text{AUNIRING}}$ is simply the logical negation of AUNIRING), respectively. Also, transistors 228 and 230 are gated by signals AUNITIP and $\overline{\text{AUNITIP}}$. Similarly, in the ventricular channel, transistors 232 and 234 are gated by signals VUNIRING and $\overline{\text{VUNIRING}}$, while transistors 236 and 238 are gated by signals VUNITIP and $\overline{\text{VUNITIP}}$. Transistors 224, 226, 228, 230, 232, 234, 236, and 238 perform the switching function previously described with reference to FIG. 3, allowing amplifiers 62 and 63 to receive tip-to-ring, tip-to-ground, or ring-to-ground signals for their respective atrial or ventricular channels. When sensing either tip-to-ground or ring-to-ground, CASE is shorted to ground, forcing tip-to-ground, ring-to-ground to be equivalent to tip-to-case, ring-to-case. The output from transconductance amplifier 62, which has a gain factor of Gm, can thus be summarized as shown in the following Table 2 for the different possible combinations of AUNIRING and AUNITIP:

TABLE 2

| AUNIRING | AUNITIP | IAEGM |
|---|---|---|
| 0 | 0 | Gm × (TIP - RING) |
| 0 | 1 | Gm × (TIP - CASE) |
| 1 | 0 | Gm × (CASE - RING) |
| 1 | 1 | Gm × (CASE - CASE) |

Similarly, for ventricular EGM transconductance amplifier 63, the output for the different possible combinations of VUNIRING and VUNITIP is summarized in the following Table 3:

TABLE 3

| VUNIRING | VUNITIP | IVEGM |
|---|---|---|
| 0 | 0 | Gm × (TIP - RING) |
| 0 | 1 | Gm × (TIP - CASE) |
| 1 | 0 | Gm × (CASE - RING) |
| 1 | 1 | Gm × (CASE - CASE) |

10-MΩ resistors 240, 242, 244, and 246, along with capacitors 216, 218, 220, and 222, form a high-pass filter network with a corner frequency of about 0.4-Hz. 9-MΩ resistors 248, 250, 252, and 254 and 14-pF capacitors 256, 258, 260, and 262 form a low-pass filter to reject high frequencies such as the 175-kHz uplink/downlink frequency. The low-pass corner frequency is at approximately 1.3-kHz in the preferred embodiment.

Differential transconductance amplifiers 62 and 63 convert the EGM differential voltages applied thereto into currents. The currents can then by easily summed for a combined atrial and ventricular EGM signal. As shown in FIG. 7, the output from atrial EGM amplifier 62 may be selectively applied to the COMBINED EGM output line by asserting an enabling signal AEGMEN that is applied to the gates of n-type transistors 264 and 266 (with the negated $\overline{\text{AEGMEN}}$ being applied to the gate of p-type transistor 268). Likewise, the output from ventricular EGM amplifier 63 may be selectively applied to the COMBINED EGM output line by asserting an enabling signal VEGMEN that is applied to the gates of n-type transistors 270 and 272 (with the negated $\overline{\text{VEGMEN}}$ being applied to the gate of p-type transistor 274). The outputs of amplifiers 62 and 63 may thus be summed by asserting both AEGMEN and VEGMEN. Of course, single channel (i.e., either atrial or ventricular) EGM signals can be provided on the COMBINED EGM output line by asserting only AEGMEN or VEGMEN.

7.5-MΩ resistor 276 and 20-pF capacitor 280 are used to turn the COMBINED EGM current signal back into a voltage, which can then be digitized and uplinked via the telemetry system. Resistor 276 and capacitor 280 are preferably selected to obtain the desired voltage range for the digitizing circuitry (not shown in the Figures), and to provide a low-pass filtering function with a corner frequency of 1-kHz. This low-pass filtering provides anti-aliasing protection for the digitizer.

In order that differenced AEGM and VEGM signals can be obtained in addition to summed AEGM and VEGM signals, switching circuits 282 and 284 have been provided. An APOS signal is applied to the gates of p-type transistors 286, 288, 290, and 292. A VPOS signal is applied to the gates of p-type transistors 294, 296, 298, and 300. As would be appreciated by those of ordinary skill in the circuit art, depending upon whether APOS or VPOS is asserted the TIP and RING signals in each channel can be reversed before they are applied to the inverting and non-inverting inputs of amplifiers 62 and 63. By inverting the sign of the output from amplifiers 62 or 63, a signal representing the difference, rather than the sum, of the atrial and ventricular sensing signals may be obtained on the COMBINED EGM output line.

Figure 8A:
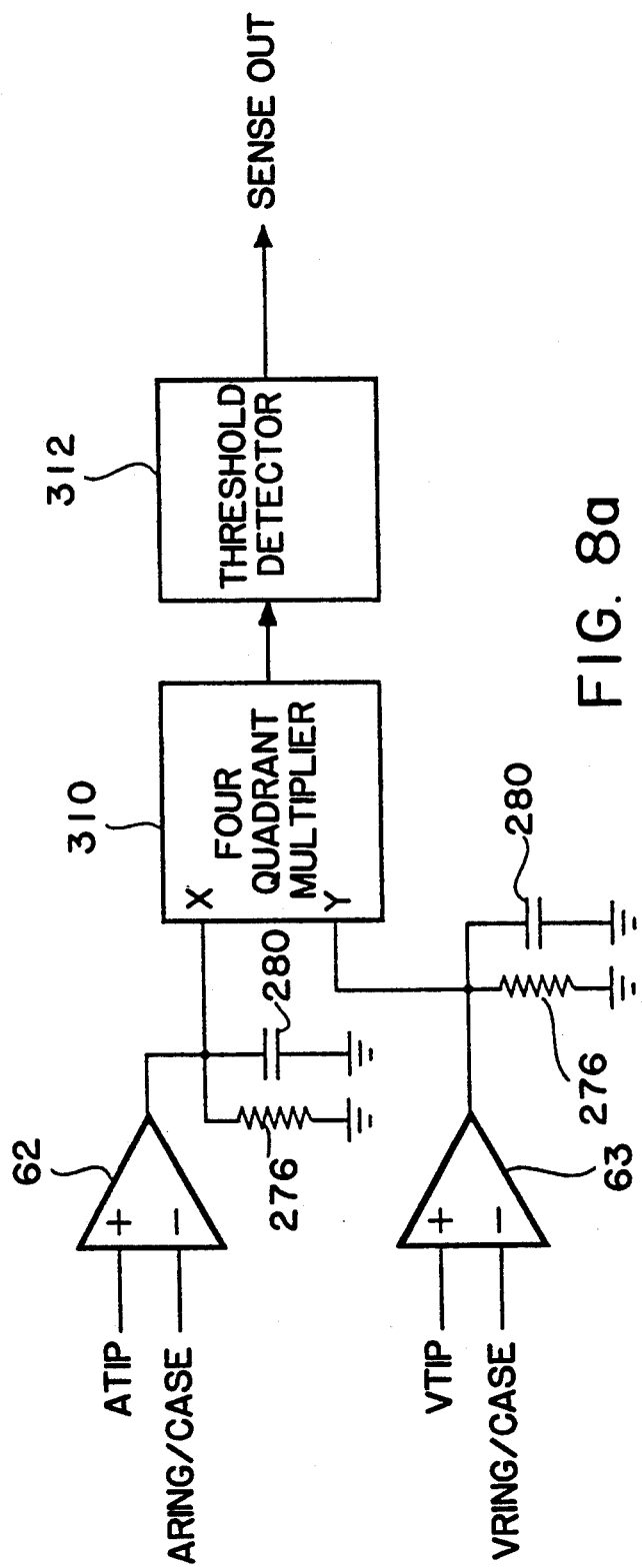
FIG. 8a is a schematic diagram of a capture verification circuit in the pacemaker of FIG. 1.

Turning now to FIG. 8a, there is shown a capture detection circuit in accordance with the presently disclosed embodiment of the invention. In the capture detection circuit of FIG. 8a a multiplier 310 having X and Y inputs is substituted in place of the current summing circuitry shown in FIG. 7. Resistor 276 and capacitor 280 are used to turn the currents from amplifiers 62 and 63 back into voltage signals. Multiplier 310 is preferably a four-quadrant analog multiplier whose output is proportional to the algebraic product of its X and Y inputs. One such multiplier which is suitable for the purposes of the present invention is the ICL8013 manufactured and commercially available from Intersil, Inc., Cupertino, Calif. Another suitable multiplier is the CA3091 manufactured and commercially available from RCA Corporation.

The output from multiplier 310 is a composite of an atrial sensing signal (either ATIP-CASE or ATIP-ARING) and a ventricular sensing signal (either VTIP-CASE or VTIP-VRING). In accordance with an important aspect of the present invention, it has been shown by the inventors that capture can be readily and reliably verified using this composite signal. In particular, the inventors have found that a sharp and distinct spike of high magnitude occurs in the composite signal when capture is achieved. Thus, verification of capture involves the simple determination of when the composite signal experiences such a spike. As shown in FIG. 8a, the this can be accomplished by applying the output from multiplier 310 to a threshold detector 312, which produces a SENSE OUT output signal whenever the input thereto exceeds a predetermined threshold voltage. It is believed by the inventors that the implementation of threshold detector 312 would be a matter of routine to a person of ordinary skill in the art, and a particular implementation of detector 312 will not be described herein in detail.

Figure 9A:
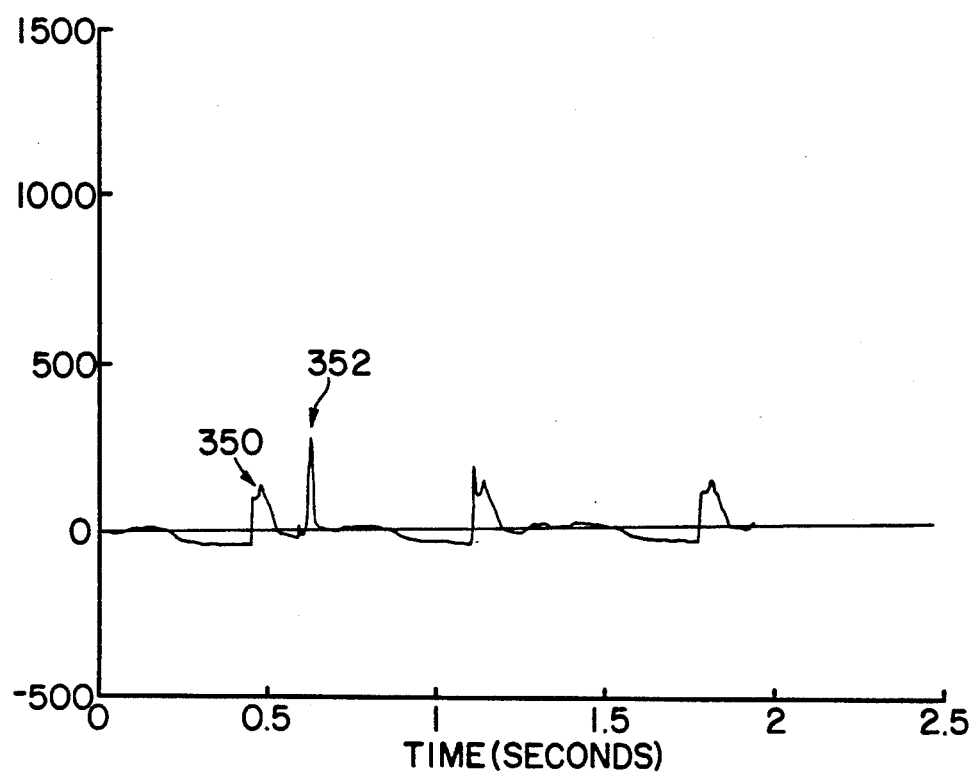
FIGS. 9a, 9b, and 9c are graphs of electrical cardiac signals illustrating capture verification in accordance with the present invention.
Figure 9B:
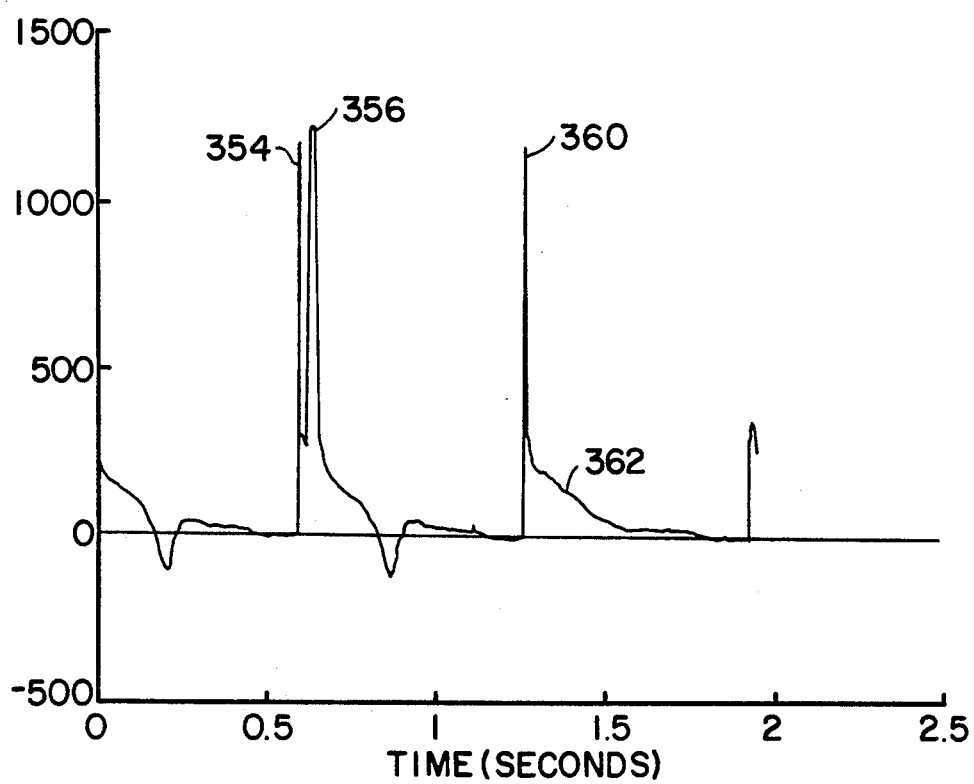
Figure 9C:
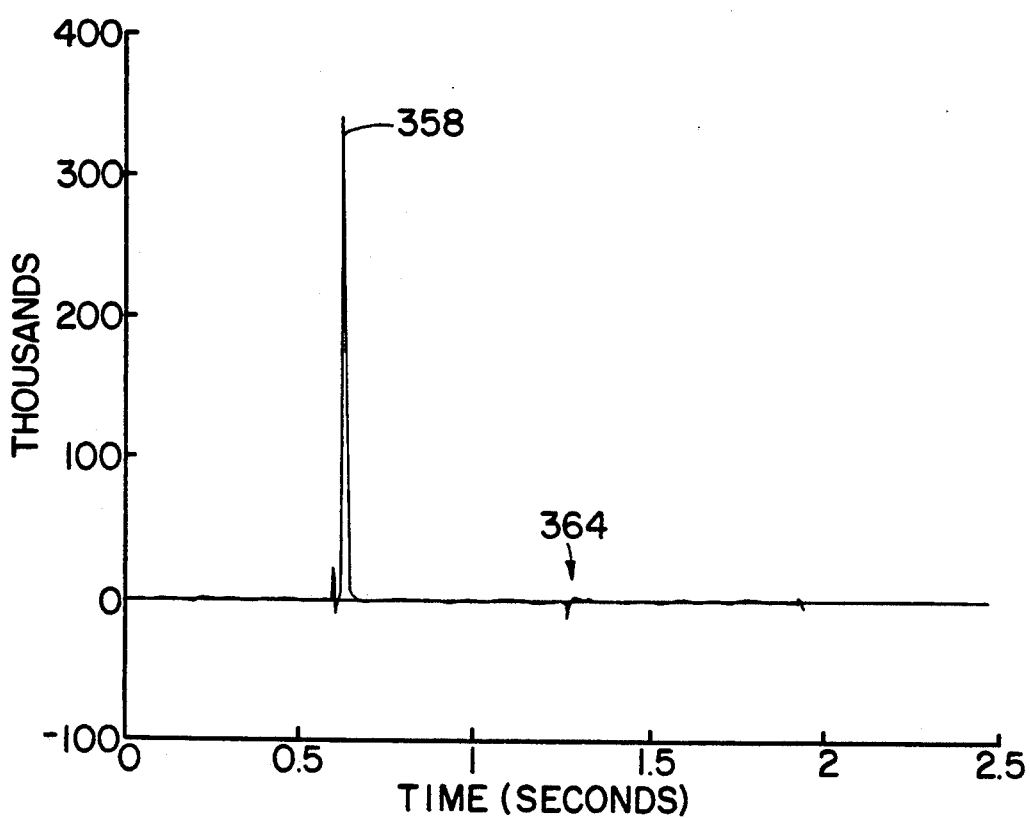

FIGS. 9a and 9b are graphs of ARING and VRING signals, respectively, in the presently disclosed embodiment of the invention. FIG. 9c is a graph of the algebraic product of ARING and VRING, i.e., ARING times VRING. It is to be understood that FIGS. 9a, 9b, and 9c have identical and aligned time scales.

In the ARING waveform of FIG. 9a, a first excursion of the ARING signal designated generally as 350 corresponds to an atrial contraction (P-wave), while a second excursion designated as 352 corresponds to detection of a ventricular contraction in the atirium, commonly called a far-field Rewave (FFR).

In the VRING waveform of FIG. 9b, a first sharp spike designated as 354 corresponds to a ventricular pacing pulse, while a second positive excursion designated as 356 is the evoked ventricular response to the pacing pulse 354.

As can be seen in the composite signal of FIG. 9c, a large positive excursion 358 results from the multiplication of the ARING and VRING signals. In accordance with an important aspect of the present invention, a positive excursion such as 358 can be used as a reliable indicator of capture.

In FIG. 9b, a sharp spike designated as 360 corresponds to a ventricular pacing pulse, while the polarization potential is designated 362. Capture is not achieved, thus no evoked response occurs at 362. The lack of capture is indicated by the small (essentially negligible) positive excursion 364 in the ARING-times-VRING waveform of FIG. 9c. Thus, as previously noted, verification of capture is accomplished by providing a simple circuit (threshold detector 312 from FIG. 8a) which is capable of distinguishing between relatively larger excursions like 358 in FIG. 9c, and relatively smaller excursions like 364 in FIG. 9c.

Figure 8B:
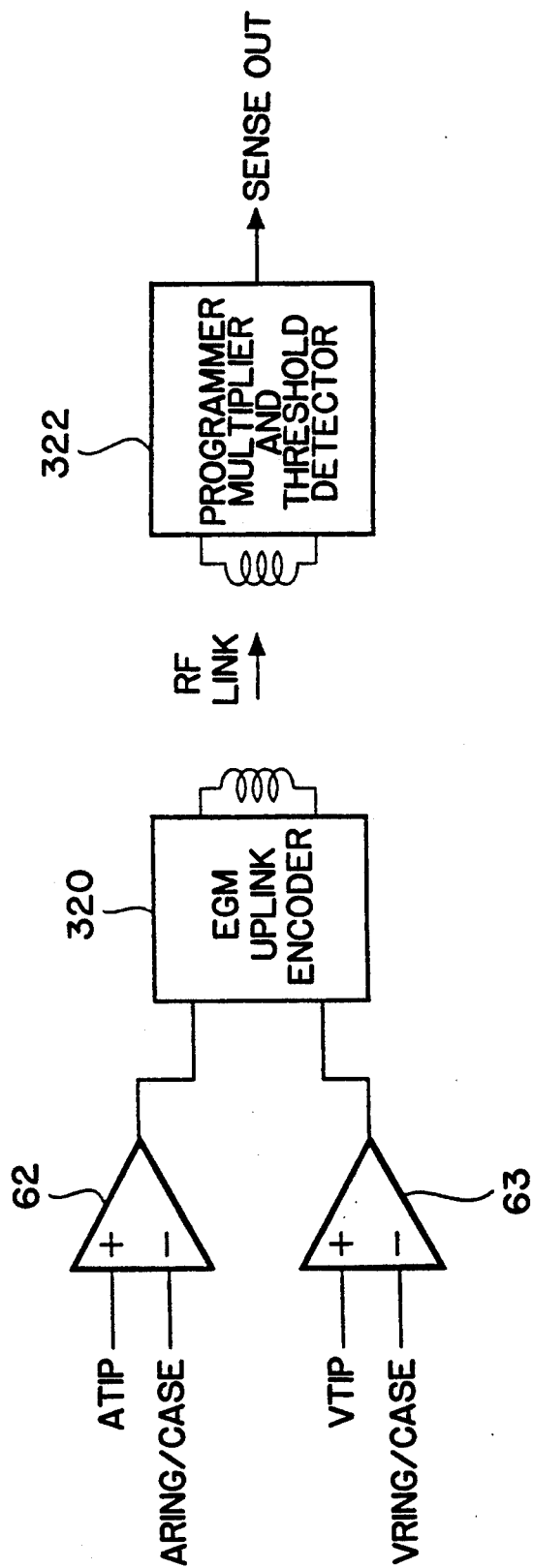
FIG. 8b is a schematic diagram of a capture verification circuit in the pacemaker and programmer system of FIG. 1b.

Although in the presently disclosed embodiment of the invention, it has been assumed that the circuitry of FIG. 8a is included inside pacemaker 10, it is contemplated by the inventors that in an alternative embodiment depicted in FIG. 8b, a portion of the circuitry of FIG. 8a could instead be included in an external programmer 322, as shown in FIGS. 1b and 8b. One such programmer suitable for the purposes of the present invention is the Medtronic Model 9760, which is capable of receiving, via telemetry, the intracardiac EGM signals. The telemetered signals could be applied to the capture detect circuitry in the programmer, and the programmer could additionally be operable to automatically adjust the pacing pulse energy based on determination of the patient's stimulation threshold. Programmer 322 could perform a threshold determination test which involves incrementally decreasing the energy of successive pacing pulses until an energy level is reached where capture is not detected. Such a threshold test is described in U.S. Pat. No. 4,250,884 issued to Hartlaub et al. on Feb. 17, 1981 entitled "Apparatus for and Method of Programming the Minimum Energy Threshold for Pacing Pulses to be Applied to a Patient's Heart", which patent is hereby incorporated by reference in its entirety. The method for stimulation threshold determination disclosed by Hartlaub et al. in the '884 patent could be characterized as semi-automatic, since the physician is required to monitor the patient's cardiac activity, such as on an ECG monitor or the like, during the threshold test, and determine visually when capture has been lost. In accordance with the present invention, however, an automatic threshold determination is possible, since the determination when capture has been lost can be performed automatically, as previously described, either by the pacemaker itself or by the external programmer.

From the foregoing detailed description of a particular embodiment of the present invention, it should be apparent that a method and apparatus for automatically verifying capture and pacing stimulation thresholds in a pacemaker patient has been disclosed. Although a particular embodiment of the present invention has been described herein in detail, it is to be understood that such description has been provided for the purposes of illustration only, and is not intended to limit the scope of the present invention as defined in the appended claims. It is believed by the inventors that various substitutions, alterations, and modifications may be made to the embodiment described herein without departing from the spirit and scope of the present invention as set forth in the claims.

What is claimed is:

1. An implantable cardiac pacemaker system comprising:
   a pulse generator, adapted to produce cardiac stimulating pulses;
   an atrial bipolar pacing/sensing lead having atrial tip and ring electrodes, a first atrial conductor therein coupled to said atrial tip electrode and a second atrial conductor therein coupled to said atrial ring electrode, said atrial tip and ring electrodes being disposed in a patient's atrium;
   a ventricular bipolar pacing/sensing lead having ventricular tip and ring electrodes, a first ventricular conductor therein coupled to said ventricular tip electrode and a second ventricular conductor therein coupled to said ventricular ring electrode, said ventricular tip and ring electrodes being disposed in said patient's ventricle;
   an indifferent electrode, disposed apart from said atrial and ventricular tip and ring electrodes;
   an atrial EGM amplifier having first and second inputs and an output, said first atrial EGM amplifier input coupled to said first atrial conductor and said second atrial EGM amplifier input coupled to said indifferent electrode, said atrial EGM amplifier adapted to generate an atrial EGM output signal corresponding to a difference between respective voltages on said first and second atrial EGM amplifier inputs;
   a ventricular EGM amplifier having first and second inputs and an output, said first ventricular EGM amplifier input coupled to said first ventricular conductor and said second ventricular EGM amplifier input coupled to said indifferent electrode, said ventricular EGM amplifier adapted to generate a ventricular EGM output signal corresponding to a difference between respective voltages on said first and second ventricular EGM amplifier inputs;
   an analog voltage multiplier having first and second inputs and an output, said multiplier coupled to said atrial EGM output and said ventricular EGM output and adapted to produce a multiplier output signal corresponding to an algebraic multiplication of said atrial EGM amplifier output signal and ventricular EGM amplifier output signal;
   a threshold detector circuit, coupled to said multiplier and adapted to produce an output pulse when said multiplier output signal exceeds a predetermined threshold.

2. A pacemaker system in accordance with claim 1, wherein said indifferent electrode comprises a conductive pacemaker canister.

3. A pacemaker system, comprising:
   a pulse generator, adapted to produce cardiac stimulating pulses;
   an atrial bipolar pacing/sensing lead having atrial tip and ring electrodes, a first atrial conductor therein coupled to said atrial tip electrode and a second atrial conductor therein coupled to said atrial ring electrode, said atrial tip and ring electrodes being disposed in a patient's atrium;
   a ventricular bipolar pacing/sensing lead having ventricular tip and ring electrodes, a first ventricular conductor therein coupled to said ventricular tip electrode and a second ventricular conductor therein coupled to said ventricular ring electrode, said ventricular tip and ring electrodes being disposed in said patient's ventricle;
   an indifferent electrode, disposed apart from said atrial and ventricular tip and ring electrodes;
   an atrial EGM amplifier having first and second inputs and an output, said first atrial EGM amplifier input coupled to said first atrial conductor and said second atrial EGM amplifier input coupled to said indifferent electrode, said atrial EGM amplifier adapted to generate an atrial EGM output signal corresponding to a difference between respective voltages on said first and second atrial EGM amplifier inputs;

a ventricular EGM amplifier having first and second inputs and an output, said first ventricular EGM amplifier input coupled to said first ventricular conductor and said second ventricular EGM amplifier input coupled to said indifferent electrode, said ventricular EGM amplifier adapted to generate a ventricular EGM output signal corresponding to a difference between respective voltages on said first and second ventricular EGM amplifier inputs;

an analog telemetry system, coupled to said atrial EGM amplifier and said ventricular EGM amplifier and adapted to transmit said atrial EGM signal and said ventricular EGM signal to an external receiving device;

a voltage multiplier, coupled to said external receiving device and adapted to multiply said transmitted atrial and ventricular EGM signals to produce a multiplied signal;

a threshold detector, coupled to said voltage multiplier and adapted to produce an output pulse when said multiplied signal exceeds a predetermined threshold.

4. A pacemaker system in accordance with claim 3, wherein said indifferent electrode comprises a conductive pacemaker canister.

5. A method for verifying that a cardiac stimulating pulse has achieved capture, comprising the steps of:
  (a) sensing an atrial signal between a transvenous atrial lead and an indifferent electrode;
  (b) sensing a ventricular signal between a transvenous ventricular lead and an indifferent electrode;
  (c) multiplying said sensed ventricular and atrial signals to produce a multiplied signal;
  (d) producing a signal indicative of capture when said multiplied signal exceeds a predetermined threshold.

* * * * *